US007901621B2

(12) United States Patent
Hafeman et al.

(10) Patent No.: US 7,901,621 B2
(45) Date of Patent: Mar. 8, 2011

(54) METHODS FOR REMOVING BIOLOGICAL RESIDUE FROM CAPILLARY WALLS IN MICROCHANNELS

(75) Inventors: Dean G. Hafeman, Hillsborough, CA (US); Aileen Zhou, San Leandro, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 747 days.

(21) Appl. No.: 11/772,744

(22) Filed: Jul. 2, 2007

(65) Prior Publication Data

US 2007/0246076 A1 Oct. 25, 2007

Related U.S. Application Data

(62) Division of application No. 10/374,759, filed on Feb. 25, 2003, now Pat. No. 7,252,928.

(60) Provisional application No. 60/363,677, filed on Mar. 12, 2002.

(51) Int. Cl.
*A61L 2/02* (2006.01)

(52) U.S. Cl. .................... 422/28; 422/1; 516/77; 516/80

(58) Field of Classification Search ........................ None
See application file for complete search history.

*Primary Examiner* — Allison M Ford

(57) ABSTRACT

Methods for removing a residue of one or more biological materials deposited on the walls of a microfluidic conduit in microscale devices are provided. In an example of the methods, one or more colloidal-size particles, such as colloidal silica particles, are flowed in a fluid within the microfluidic conduit having residues of materials previously deposited on the walls thereof to adsorb to the materials and to remove such deposits from the walls of the microfluidic conduit.

14 Claims, 2 Drawing Sheets

METHODS FOR REMOVING BIOLOGICAL RESIDUE FROM CAPILLARY WALLS IN MICROCHANNELS

This application is a divisional of U.S. patent application Ser. No. 10/374,759 filed Feb. 25, 2003, and claims the benefit of U.S. Provisional Patent Application No. 60/363,677, filed Mar. 12, 2002, both of which are incorporated herein by reference.

BACKGROUND OF THE INVENTION

Surface adsorption of biological materials, such as proteins, to the walls of microscale fluid conduits can cause a variety of problems. For example, in assays relying on flow of material in the conduits, adsorption of test or reagent materials to the walls of the conduits (or to reaction chambers or other microfluidic elements) can cause generally undesirable biasing of assay results.

For example, charged biopolymer compounds can be adsorbed onto the walls of the conduits, creating artifacts such as peak tailing, loss of separation efficiency, poor analyte recovery, poor retention time reproducibility and a variety of other assay biasing phenomena. The adsorption is due, in part, e.g., to electrostatic interactions between, e.g., positively charged residues on the biopolymer and negatively charged groups resident on the surface of the separation device.

Reduction of surface adsorption in microscale applications is typically achieved by coating the surfaces of the relevant microscale element with a material which inhibits adsorption of assay components. For example, glass and other silica-based capillaries utilized in capillary electrophoresis have been modified with a range of coatings intended to prevent the adsorption of charged analytes to the walls of the capillaries. See, for example Huang et al., J. Microcol. Sep. 4, 135-143 (1992); Bruin et al., Journal of Chromatogr., 471, 429-436 (1989); Towns et al., Journal of Chromatogr., 599, 227-237 (1992); Erim, et al., Journal of Clromatogr., 708, 356-361 (1995); Hjerten, J. Chromatogr., 347, 191 (1985); Jorgenson, Trends Anal. Chem. 3, 51 (1984); and McCormick, Anal. Chem., 60, 2322 (1998). These references describe the use of a variety of coatings, including surface derivatization with poly(ethyleneglycol) and poly(ethyleneimine), funictionalization of poly(ethyleneglycol)-like epoxy polymers as surface coatings, functionalization with poly(ethyleneimine) and coating with polyacrylamide, polysiloxanes, glycerolglycidoxypropyl coatings and others. Surface coatings have also been used for, e.g., modification of electroosmotic potential of the relevant microscale surface e.g., as taught in U.S. Pat. No. 5,885,470, CONTROLLED FLUID TRANSPORT IN MICROFABRICATED POLYMERIC SUBSTRATES by Parce et al.

Other than the use of surface coatings, few approaches exist for controlling surface adsorption of biopolymers in microscale systems. In general, other design parameters used to control adsorption include the material used in the device, modulation of flow rates and the like. Generally, surface adsorption of biological materials in capillary fluidics applications is a significant issue for at least some applications, and additional mechanisms for inhibiting surface adsorption in microfluidic applications are desirable. The present invention provides new strategies for inhibiting surface adsorption of polymers, molecules and biological materials, e.g., in pressure-based microscale flow applications. Additional features will become apparent upon complete review of the following disclosure.

SUMMARY OF THE INVENTION

The present invention derives from the surprising discovery that surface adsorption of biological materials to the walls of microfluidic channels can be largely eliminated by flowing one or more colloidal-size particles through a fluid in the microfluidic conduit. The colloidal particles adsorb to the surface of the materials such as to prevent their binding to the capillary walls of the microfluidic conduits. The materials such as macromolecules (e.g., proteins, digopeptides, complex carbohydrates, lipids, oligonucleotides, ligands and the like) bind to the surface of colloidal particles instead of the capillary walls, thereby allowing "sticky" macromolecules to flow through the conduits without fouling. The inventors have found that active enzymes such as protein enzymes may be adsorbed onto the surface of the colloidal particles while retaining enzymatic activity. Thereby the active enzyme may be introduced into microfluidic channels without the risk of sticking to the channel walls. Adsorption of a variety of materials can be regulated by the application of the principles of the present invention, including proteins, cells, carbohydrates, nucleic acids, lipids and a combination thereof.

In one aspect of the invention, a method of reducing adsorption of one or more materials to an interior surface of a microchannel is disclosed which comprises flowing the one or more materials in a fluid in the microchannel, and concomitantly flowing a colloidal material such as colloidal particles through the fluid in the microchannel at a sufficient concentration to bind to the one or more materials and thereby prevent the materials from binding to the interior surface of the microchannel. The colloidal material may be present in the fluid at a concentration of between about 0.0001 and 1% by volume, for example. For example, the colloidal material (e.g., colloidal particles) may be present in the fluid at a concentration of greater than about 0.024% by weight, for example greater than about 0.003% by weight, for example between about 0.003 and 0.024% by weight, in order to prevent the material (such as macromolecules) from binding to an interior surface of the microchannel. In one aspect of the invention, the concentration of colloidal particles in the fluid in the microchannel is such that a surface area of the particles contained in a given volume of the fluid is at least equal to or greater than a surface area of the microchannel, for example, equal to about ten times (or more) the surface area of the microchannel In another aspect of the invention, colloidal particles as described above may be introduced into microfluidic channels having residues of materials, such as macromolecules, previously deposited on the walls thereof, and will bind to the materials to remove such deposits and leave the wall surfaces free of the deposits.

In addition, adsorption prevention agents can also be used alone or in combination with the use of colloidal particles to further reduce unwanted adsorption, including, e.g., detergents (ionic or nonionic) and blocking agents (e.g., high molecular weight polymers such as polyethylene glycols, polyethers, or the like, or alternatively proteins such as caseins, albumins (e.g., BSA or the like), high ionic strength or high concentrations of zwitterionic compounds such as betaine, and nonaqueous solvents, such as ethanol, methanol, dimethlysulfoxide (DMSO) or dimethylformamide (DMF) or the like. These adsorption prevention agents can be used in place of or in concert with application of colloidal particles for reduction of surface adsorption. In addition, application of an electric field in a fluidic conduit during pressure-based flow can help prevent or reduce adsorption of materials from adhering to the walls of the microfluidic conduits as is more fully described in copending patent application Ser. No. 09/310,027 assigned to the assignee of the present invention and entitled "Prevention of Surface Adsorption in Microchannels by Application of Electric Current During Pressure-Induced Flow," filed May 11, 1999, the entire contents of which are incorporated by reference herein.

The methods of the present invention are particularly applicable for use in microfluidic devices and systems having channels with microscale dimensions in which issues of surface adsorption of biological sample materials to the walls of such channels are particularly problematic, although the methods described herein are not necessarily limited to such devices and systems. Microfluidic devices and systems generally include a body having one or a plurality of fluidly coupled microchannels disposed therein. A source of fluidic material is fluidly coupled to at least one of the plurality of microchannels. A fluid pressure controller is fluidly coupled to the at least one microchannel and, in most systems, at least two electrodes are in fluidic or ionic contact with the at least one microchannel. An electrical controller is typically in electrical contact with the at least two electrodes.

In general, the device or system can be configured for electrokinetic, electrophoretic or pressure-based flow, or a combination of the same. For example, flow can be primarily driven by pressure with a small or negligible contribution by electrokinetic forces, or, optionally, the electrokinetic forces can contribute similar or even greater velocity to a material or fluid than the pressure-based forces. In one aspect, the electrical controller is configured to minimize movement of the fluidic material in a direction of fluid flow, or to minimize movement of charged fluidic material in the direction of flow of the charged material. Typically, the fluid pressure controller and the electrical controller concomitantly apply a fluid pressure gradient and an electric field in the at least one channel. Thus, the device or system can include a control element such as a computer with an instruction set for simultaneously regulating electrical current and fluidic pressure in the at least one channel (or any other microscale element in the device). The body of the device or system is typically fabricated from one or more material(s) commonly used in microscale fabrication, including ceramics, glass, silicas, and plastics or other polymer materials. The microscale elements (e.g., microchannels) within the body structure typically have at least one dimension between about 0.1 and 500 microns, for example, a depth of between about 1 and 100 microns and a width of between about 10 and 200 microns. Ordinarily, the body has a plurality of intersecting microchannels formed into a channel network.

The device or system will ordinarily include a signal detector mounted proximal to a signal detection region, fluidly coupled to the at least one microchannel. This detector can be configured to monitor any detectable event, e.g., an optical, thermal, potentiometric, radioactive or pH-based signal.

There are a variety of microfluidic devices and systems which can be used with the present invention. For example, Ramsey WO 96/04547 provides a variety of microfluidic systems. See also, Ramsey et al. (1995), *Nature Med.* 1(10): 1093-1096; Kopf-Sill et al. (1997) "Complexity and performance of on-chip biochemical assays," *SPIE* 2978:172-179 February 10-11; Bousse et al. (1998) "Parallelism in integrated fluidic circuits," *SPIE* 3259:179-186; Chow et al. U.S. Pat. No. 5,800,690; Kopf-Sill et al. U.S. Pat. No. 5,842,787; Parce et al., U.S. Pat. No. 5,779,868; Parce, U.S. Pat. No. 5,699,157; Parce et al. WO 98/00231 Parce et al. WO 98/00705; Chow et al. WO 98/00707; Parce et al. WO 98/02728; Chow WO 98/05424; Parce WO 98/22811; Knapp et al., WO 98/45481; Nikiforov et al. WO 98/45929; Parce et al. WO 98/46438; Dubrow et al., WO 98/49548; Manz, U.S. Pat. No. 5,296,114 and e.g., EP 0 620 432 A1; Seiler et al. (1994) *Mitt Gebiete Lebensm. Hyg.* 85:59-68; Seiler et al. (1994) *Anal. Chem.* 66:3485-3491; Jacobson et al. (1994) "Effects of Injection Schemes and Column Geometry on the Performance of Microchip Electrophoresis Devices" *Anal. Chem.* 66: 66. 1107-1113; Jacobsen et al. (1994) "Open Channel Electrochromatograpy on a Microchip" *Anal. Chem.* 66:2369-2373; Jacobsen et al. (1994) "Precolumn Reactions with Electrophoretic Analysis Integrated on Microchip" *Anal. Chem.* 66:4127-4132; Jacobsen et al. (1994) "Effects of Injection Schemes and Column Geometry on the Performance of Microchip Electrophoresis Devices." *Anal. Chem.* 66:1107-1113; Jacobsen et al. (1994) "High Speed Separations on a Microchip." *Anal. Chem.* 66:1114-1118; Jacobsen and Ramsey (1995) "Microchip electrophoresis with sample stacking" Electrophoresis 16:481-486; Jacobsen et al. (1995) "Fused Quartz Substrates for Microchip Electrophoresis" *Anal. Chem.* 67: 2059-2063; Harrison et al. (1992) "Capillary Electrophoresis and Sample Injection Systems Integrated on a Planar Glass Chip." *Anal. Chem.* 64:1926-1932; Harrison et al. (1993) "Micromachining a Miniaturized Capillary Electrophoresis-Based Chemical Analysis System on a Chip." *Science* 261: 895-897; Harrison and Glavania (1993) "Towards Miniaturized Electrophoresis and Chemical System Analysis Systems on Silicon: An Alternative to Chemical Sensors." *Sensors and Actuators* 10:107-116; Fan and Harrison (1994) "Micromachining of Capillary Electrophoresis Injectors and Separators on Glass Chips and Evaluation of Flow at Capillary Intersections. *Anal. Chem.* 66: 177-184; Effenhauser et al. (1993) "Glass Chips for High-Speed Capillary Electrophoresis Separations with Submicrometer Plate Heights" *Anal. Chem.* 65:2637-2642; Effenhauser et al. (1994) "High-Speed Separation of Antisense Oligonucleotides on a Micromachined Capillary Electrophoresis Device." *Anal. Chem.* 66:2949-2953; and Kovacs EP 0376611 A2.

Definitions

Unless specifically indicated to the contrary, the following definitions supplement those in the art for the terms below.

"Microfluidic," as used herein, refers to a system or device having fluidic conduits or chambers that are generally fabricated at the micron to submicron scale, e.g., typically having at least one cross-sectional dimension in the range of from about 0.1 μm to about 500 μm. The microfluidic systems of the invention are fabricated from materials that are compatible with components of the fluids present in the particular experiment of interest. Customarily, such fluids are substantially aqueous in composition, but may comprise other agents or solvents such as alcohols, acetones, ethers, acids, alkanes, or esters. Frequently solvents such as DMF or DMSO are used, either pure, or in aqueous mixture, to enhance the solubility of materials in the fluids. In addition, the conditions of the fluids are customarily controlled in each experiment.

Such conditions include, but are not limited to, pH, temperature, ionic compositions and concentration, pressure, and application of electrical fields. The materials of the device are also chosen for their inertness to components of the experiment to be carried out in the device. Such materials include, but are not limited to, glass and other ceramics, quartz, silicon, and polymeric substrates, e.g., plastics (such as polymethyhnethacrylate (PMMA) or polydimethylsiloxanes (PDMS)), depending on the intended application.

A "microchannel" is a channel having at least one microscale dimension, as noted above. A microchannel optionally connects one or more additional structures for moving or containing fluidic or semi-fluidic (e.g., gel- or polymer solution-entrapped) components.

A "microwell plate" is a substrate comprising a plurality of regions which retain one or more fluidic components.

A "pipettor channel" is a channel in which components can be moved from a source to a microscale element such as a second channel or reservoir. The source can be internal or external (or both) to the main body of a microfluidic device comprising the pipettor channel.

DETAILED DISCUSSION OF THE INVENTION

Figure 1:
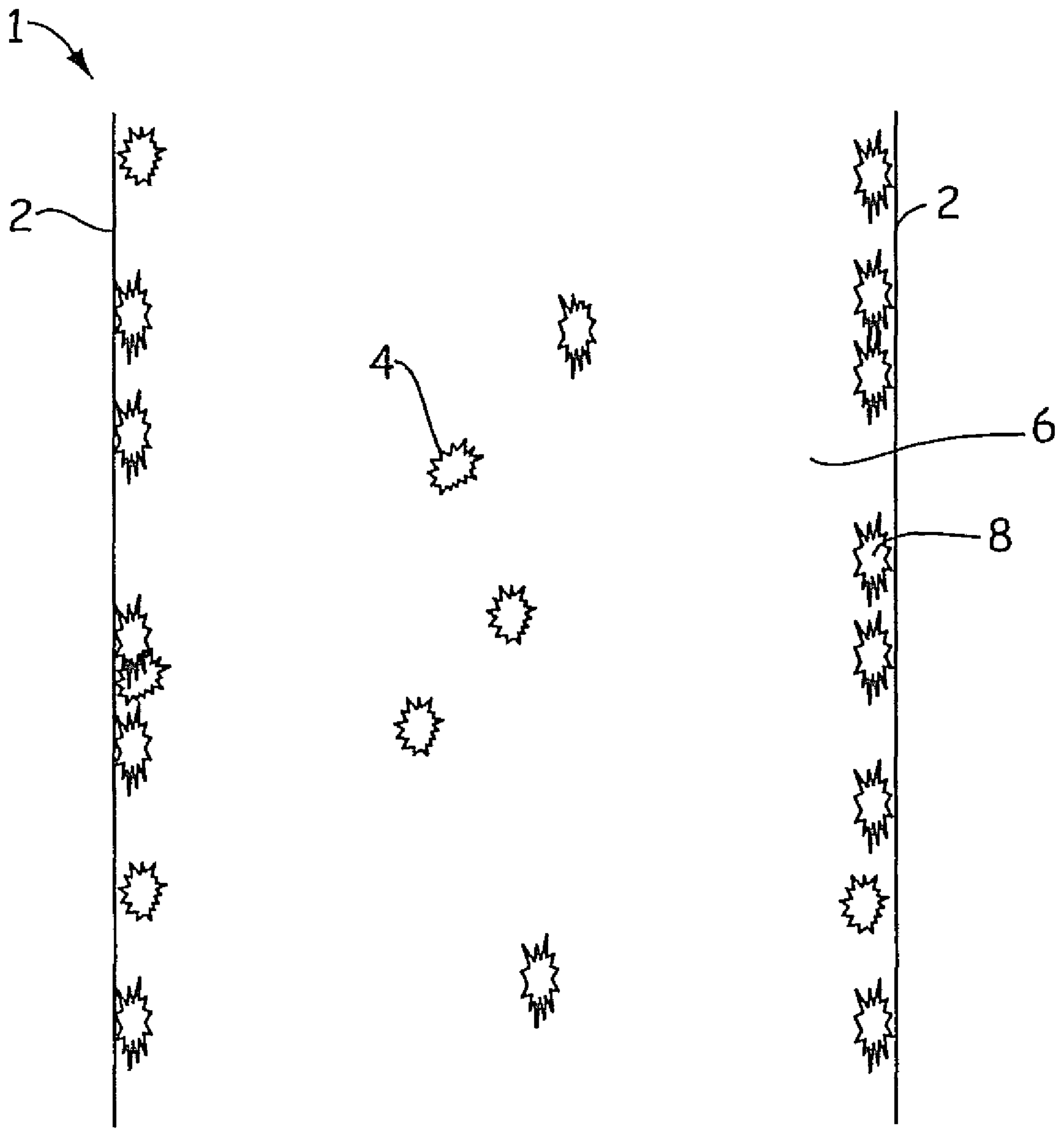
FIG. 1 is a schematic illustration of a microchannel having flowing (free) and adsorbed macromolecules bound to the walls of the microchannel.

The invention relates to the reduction and prevention of surface adsorption of materials to microchannel walls and other microscale elements in microfluidic systems. It was determined that binding to the surface of microscale elements was particularly problematic in flowing assays and material separations for proteins, cells, carbohydrates, nucleic acids, lipids and other materials during pressure-based flow of the materials through conduits fabricated from a variety of materials. This was due, in part, to the fact that the rate of flow (flow velocity) of materials at the walls in a microscale channel typically is lower than the rate of flow of the materials in the interior of the microscale channel. This low flow rate increases the time that a material remains in position proximal to a given surface of the microscale channel. Without being bound to a particular theory of generation, it is believed that this increased proximity to a single region can lead to formation of strong interactions between the channel surface and the material.

In contrast, in electroosmotic flow systems, maximal material velocity is ordinarily achieved at the walls of the microscale channels, typically at about 10 -15 Å from the surface of the wall. The diameter of many biological materials is large with respect to this distance. For purposes of this disclosure, the diameter of a material is "large" with respect to this distance when the average diameter of the material is at least about 5 Å, typically at least about 10 Å, often at least about 20 Å, generally at least about 50 Å or more in diameter. For example, the diameter of the protein hemoglobin is about 55 Å, and is "large" with respect to a measurement of 10-15 Å. Large biological molecules such as cells are, of course, large as compared to the region of maximal flow velocity.

Data suggest that the linetics of surface adsorption during flow for many materials includes several steps. First, a low affinity association occurs between the material and a wall of a conduit through which the material is being flowed. This low affinity association is relatively short in duration and is followed by a higher affinity interaction that is relatively longer lived. This higher affinity interaction can give way to an even higher affinity interaction in which the material becomes essentially permanently adhered to the surface. In this state, the material can exist in a denatured, or at least in a non-solution phase state. Once the material achieves the high affinity interaction, it is difficult to displace from the wall of the conduit.

Because of the flow profile during pressure-based flow, the velocity of many biological and other materials is close to zero at the wall of a microscale conduit during pressure-based flow. It is theoretically believed that this low flow velocity provides time for high affinity binding between the material and the wall of the conduit to occur. To counteract the tendency of biological materials to adhere to the walls of microfluidic conduits, the inventors have discovered that colloidal-size particles can be used in the microfluidic channel to provide an alternative molecular surface to which the biological materials can adhere. The colloidal particles are administered through a fluid in the microfluidic channel, and the biological materials present in the channel tend to adsorb to the surface of the materials such as to prevent their binding to the capillary walls of the channels. The materials such as macromolecules (e.g., proteins, complex carbohydrates, oligonucleotides, ligands and the like) bind to the surface of colloidal particles instead of the capillary walls, thereby allowing "sticky" macromolecules to flow through the conduits without fouling the same. The inventors have found that active enzymes such as protein enzymes may be adsorbed onto the surface of the colloidal particles while retaining enzymatic activity and mobility through conduits. Thereby the active enzyme may be introduced into microfluidic channels without the risk of sticking to the channel walls.

Colloidal particles are generally defined to be particles having a major dimension in the range of about 1 millimicron to about 1 micron. Colloidal particles may be gaseous, liquid, or solid, preferably solid, and occur in various types of suspensions. Generally speaking, colloidal particles have a surface area that is so large with respect to their volume that the particles do not settle out of the suspension by gravity even if the density of the particles is substantially greater than that of the suspending fluid.

Further, the particles are small enough to pass through filter membranes such as 0.22 or 0.45 micron filters used for sterile biological media. Macromolecules, i.e., proteins and other high polymers such as carbohydrates, are usually thought to be at the lower limit of the above range for particles of colloidal dimension. In terms of the present invention, "colloidal particles" is intended to include organic and inorganic particles of the indicated dimension. An example of colloidal particles to be used with the present invention includes colloidal silica particles. The colloidal silica particles preferably have a relatively high surface area on the order of about 200 square meters per gram of solid particle, for example, about 220 square meters per gram of solid.

Other examples of colloidal particles include colloidal alumina, silicon nitride, magnesium oxide, and the like. Also, zeolites or other naturally occurring mineral powders or mineral precipitates may be used. The colloidal particles also may include organic polymer colloids including polyethylenes, polystyrenes, or other latex particles. In general the colloids used in the instant invention will be lyophobic colloids, i.e. particles insoluble in the solvent. Essential to such lyophobic colloids are the presence of stabilizing conditions or substances. For example, colloidal silica in aqueous systems generally requires a pH value greater than 7.0 so that a significant number of surface silanol groups are ionized, giving the particles a substantial negative charge. The coulombic repulsion of the particles, one from another, thereby stabilizes the suspension. Other means of stabilizing such lyophobic colloidal suspensions include adsorption of polymers or detergents that bear either positive or negative charge. Alternatively, the polymers or detergents may be nonionic, or relatively uncharged, instead bearing chemical moieties that are polar, or otherwise highly soluble in aqueous media, for example by containing many hydroxyl moieties. Thereby coating of fine water-insoluble powders such as mineral carbonates, chlorides, chromates, cyanates, fluorides, hydroxides, iodates, oxalates, phosphates, sulfates, sulfides, or thiocyanates with a water-soluble detergent or polymer, such as polyethylene oxide, will convert such lyophobic powders into stabile lyophobic colloidal systems suitable for use in the instant invention. Additional means for stabilizing such colloidal systems for use in the instant invention may be found in the Handbook of Surface and Colloid Chemistry, Edited by K. S. Birdi, (1997), published by CRC Press, New York, which is herein incorporated by reference.

Macromolecules may bind to the surface of the colloidal particles by one, or more, of several mechanisms. The colloidal particles often bear a substantial electrical charge, due to the presence of ionized surface groups. Thus macromolecules, of opposite charge, or localized regions of charge within the macromolecules may be bound to the colloidal particles by coulombic attraction. Alternatively, the particles may bear at least regions of hydrophobic character, for example due to the presence of aliphatic groups. Macromolecules with hydrophobic character, or regions of hydrophobic character will adsorb to such colloidal particles by hydrophobic interaction. Further, a first member of a specific ligand or binding pair, such as an antibody, hapten, lectin or other receptor may be attached to the surface of the colloidal particles to offer specific attachment of macromolecules having sites complementary to the specific ligands. Thus, the first member of the specific binding pair may be attached to the colloidal particle and the complementary, or second member of the binding pair, incorporated or attached to the macromolecule. A well-known example of such a binding pair where the first member has an extremely high affinity for the second member of the pair is avidin (or streptavidin) and biotin. Methods for attachment of biotin and avidin (or streptavidin), and like receptors to surfaces are well-know to those skilled in the art and may be found in references, such as The Handbook of Fluorescent Probes and Research Chemicals, $6^{th}$ Ed., by Richard Haugland; Molecular Probes, Eugene, Oreg. and references contained therein.

The colloidal particles generally will be used at a given concentration sufficient to bind to materials suspended in a liquid or fluid that is to be delivered into a microchannel. As described in greater detail below with reference to the Examples, the concentration of the particles suspended in the liquid preferably will be such that the surface area of the particles contained in a given volume of liquid is equal to, or greater than, the surface area of a microchannel needed to contain the liquid volume, for example, equal to about ten times (or more) the surface area of the microchannel. It has been observed that little or no enzyme activity was present on the interior surface of a microchannel when the colloidal particles are present in the fluid at a concentration of at least about 0.003% by weight, for example between about 0.003 to 0.024% by weight, for example greater than about .024% by weight, or for example between about 0.0001 to about 1% by volume. If the particles are diluted by merging with fluid streams without the particles, then the original concentration of particles should be correspondingly increased by the dilution factor so as to keep the particle surface area in excess of the channel surface area. For example, for a 10-fold dilution performed in a microfluidic channel, would then dictate that the particle concentration should be increased by a factor of about 10. It should be understood that the concentration of colloidal particles sufficient to bind to materials present in a fluid in the microchannel may vary depending on the type of materials present in the microchannel and other features of the materials (such as the surface area and volume of material present in the fluid).

Figure 2:
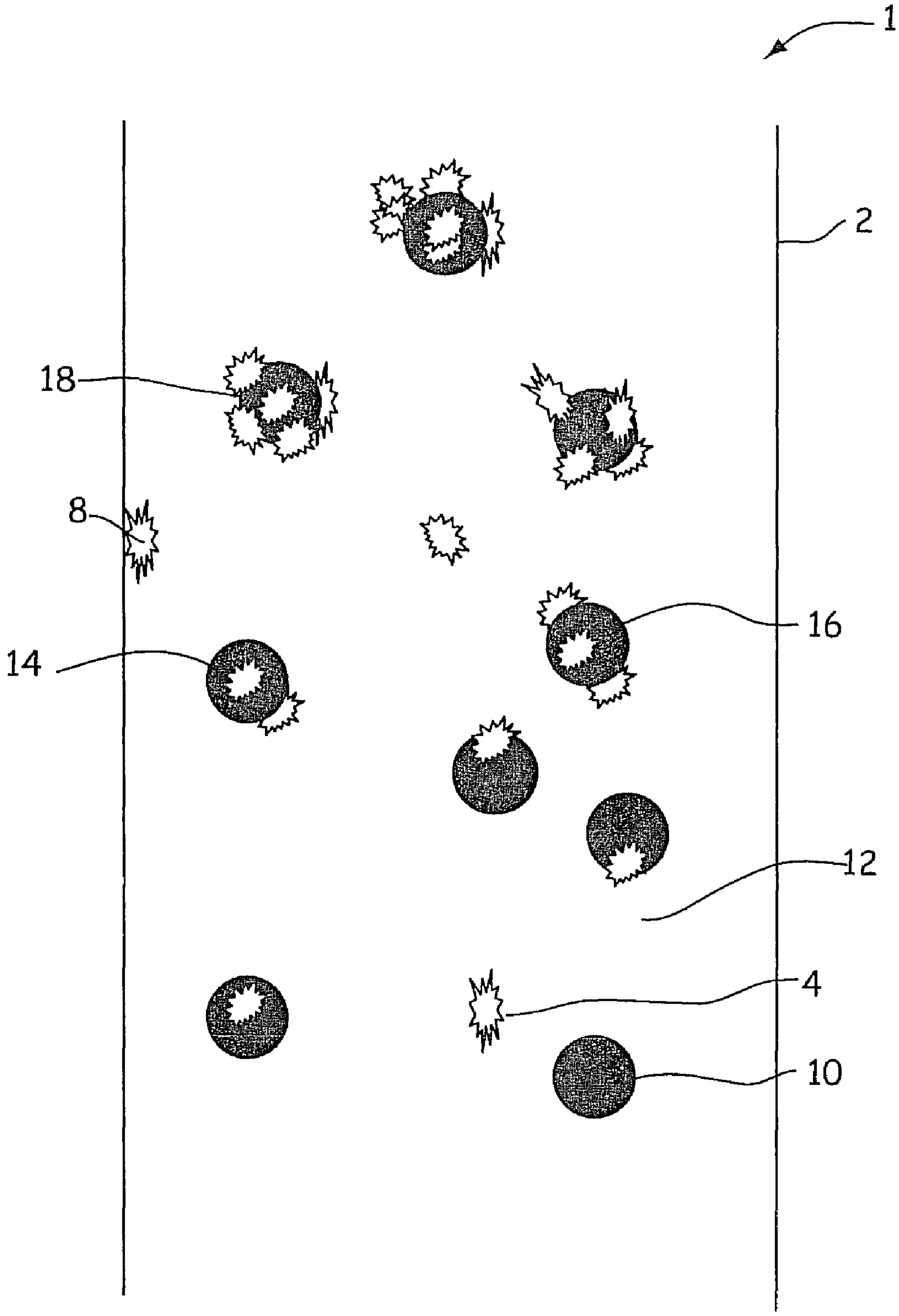
FIG. 2 is a schematic illustration of the microchannel of FIG. 1 having a plurality of colloidal particles flowing through the microchannel and shown adsorbed to the surface of a plurality of the macromolecules of FIG. 1.

In another aspect of the invention, colloidal particles as described above may be introduced into microfluidic channels having residues of materials (such as enzyme activity) previously deposited on the walls thereof and will bind to the materials to remove such deposits and leave the wall surfaces free of the deposits The teachings of the present invention can be generally understood with reference to FIGS. 1 and 2. As shown in FIG. 1, the microchannel walls 2 of a microchannel 1 offer a large surface area for the binding of free biological materials, e.g., macromolecules 4 dissolved or suspended within fluids 6 flowing within the channel walls. Bound to the surface of the microchannel walls are macromolecules 8 which are thereby immobilized or stationary to flow within the microchannel. The ratio of immobilized macromolecules 8 to free macromolecules 4 in the microchannel can often be very high, often exceeding 1 and sometimes exceeding 10, 100 or 1000, for example. When transport of the macromolecules through the cha nnels is desired, immobilization of the macromolecules to the channel walls can be highly problematic and can generally cause undesirable biasing of assay results.

As shown in FIG. 2, colloidal particles 10 that are typically larger in diameter than the minimum diameter of the macromolecules 4, but smaller in diameter than the distance between the microchannel walls 2, will easily flow as a fluid within the walls. The colloidal particles may be continuously or periodically administered into the fluid in the microchannel to bind to the materials present in the fluid and thus prevent such materials from binding to an interior surface of the microchannel. Further, provided that the colloidal particles have a substantial affinity for the macromolecules, the macromolecules will adsorb to surfaces of the colloidal particles 10 and thereby remain suspended within the fluid 6 and substantially free of immobilization to the microchannel walls 2. The colloidal particles with bound macromolecules may be present as an ensemble of particles comprising particles with one bound macromolecule 12, for example, or two, three, or four of more bound macromolecules 14, 16, and 18 respectively. Together with the totally free macromolecule species 4, the ensemble forms of particle-bound macromolecules 12-18, are free to move with the suspending fluid 6 within the microchannel walls 2. Preferably, the ratio of immobilized macromolecules, to mobile macromolecules, is less than 1, and often less than 0.1, 0.01, or 0.001, for example.

In addition to the use of colloidal particles to prevent adsorption of materials to walls of conduits, additional adsorption prevention agents can also be used to reduce unwanted adsorption, including, the use of adsorption prevention agents such as detergents (NDSB, Triton x-100, SDS, etc.) and blocking agents (e.g., high molecular weight polymers such as polyethylene glycols, polyethers, or the like, or alternatively proteins such as caseins, albumins (e.g., BSA or the like) and reconstituted non-fat dry milk) to reduce surface adsorption of materials of interest. These adsorption prevention agents can be used in concert with, or separate from the use of colloidal particles to prevent adsorption of materials to microscale structures. Typically, the concentration of detergent is about 0.05 M to 1 M (typically about 0.1 M) and the concentration of blocking protein is about 0.05 mg/ml to 1 mg/ml, typically about 0.1 mg/ml.

In addition, other adsorption inhibition agents can be used alone or in combination with the use of colloidal particles, including high ionic strength or high concentrations of zwitterionic compounds such as betaine, and nonaqueous solvents, such as ethanol, methanol, dimethlysulfoxide (DMSO) or dimethylformamide (DMF) or the like. In addition, application of electric fields, such as an alternating electric current, can be applied to biological materials under pressure-induced flow for reduction of surface adsorption as described in more detail in copending patent application Ser. No. 09/310,027, entitled "Prevention of Surface Adsorption in Microchannels by Application of Electric Current During Pressure-Induced Flow," filed on May 11, 1999, and previously incorporated by reference herein.

A variety of approaches are appropriate for monitoring surface adsorption of selected biological materials in microfluidic systems and any available method for measuring adsorption of materials to microfluidic system elements can be adapted to the present invention. The precise methodology appropriate to monitoring reduced surface adsorption depends on the material at issue. Where materials can be viewed optically (e.g., using a microscope), such as where the materials are cells, adsorption can be directly monitored by simply viewing a portion of the channel through which the material is flowed. Adsorption is characterized by immobilization of the material in a region of the channel. Materials such as proteins and nucleic acids can be made viewable by incorporation of labels such as fluorophores, radioactive labels, labeled antibodies, dyes and the like, and can similarly be directly monitored by detecting label signal levels in a portion of the channel.

In addition to direct detection methods, indirect adsorption detection methods are also appropriate. For example, controls comprising assay elements for a control assay can be flowed through a channel and the results of the assay monitored and compared to expected results. Where the results of the assay are not as predicted (e.g., where enzyme concentration appears to increase constantly over time), or change markedly over time, it can be inferred that adsorption is interfering with the assay components. If the assay components are similar in nature to those being tested (e.g., where both the control and test elements are proteins) it can be inferred that adsorption is interfering with the test components as well.

EXAMPLES OF USE OF COLLOIDAL PARTICLES AS ADSOROTION PREVENTION AGENTS

Example 1

An assay screen is performed to identify inhibitors of an enzymatic reaction. An example of a microfluidic assay chip to be used is the nucleic acid (e.g., DNA) LabChip® microfluidic chip device which is commercially available from Caliper Technologies Corp., for example. Colloidal silica particles were purchased as a 30% (by weight) from Aldrich Chemical Company (Milwaukee, Wis.) as Ludox® AM-30 colloidal silica particles (catalog no. 42,084). These particles have a very high surface area of approximately 220 square meters per gram of solid. This suspension was diluted 1:1 with pH 7.5 sodium HEPES buffer with 5 nM MgC,l and then mixed with equal volume of 1.22 micromolar solution of protein kinase-A-β enzyme (PKA-β) in the same buffer. The mixture containing enzyme and 7.5% colloidal silica was placed into one or more enzyme reservoir wells of the microfluidic assay chip. Into one or more other wells of the assay chip the same amount of enzyme was added without the colloidal silica particles. Next a standard on-chip mobility shift assay screen for inhibitors of (PKA-β) was performed using Mg-ATP and a fluorescein-labeled peptide as substrates.

A standard inhibitor of PKA-β enzyme (H-89) was placed at the same concentration in multiple wells in a 96-well microplate and sipped by a pipettor channel coupled to the assay chip in an integrated microfluidic instrument system (e.g., the Caliper® 250 HTS System or AMS 90 SE Electrophoresis System, both commercially available from Caliper Technologies Corp.) in order to show enzyme activity and inhibition of the enzyme by the inhibitors. All four channels showed similar enzyme activity and inhibition by the H-89 inhibitor.

At the conclusion of a series of such inhibitor assays, each of the microchannels were checked for sticking of active enzyme material to the microchannel surfaces by removing the enzyme (by repeated aspiration and rinsing with the buffer) from the enzyme wells. The microchannels without the colloidal particles (in the enzyme well) showed the presence of residual enzyme activity (about the same as when enzyme was present in the wells). In contrast the channels with the colloidal particles showed no detectable enzyme activity. Thus the colloidal particles substantially prevented the retention of enzyme activity on the walls of the microfluidic microchannels.

Example 2

Ludox AM-30 colloidal particles (0.006 micron particle radius) were utilized in a microfluidic chip having channels similar to that employed in Example 1 above. In order to understand the shape of the channels (and thus the surface/volume ratio) it is useful to understand the method used to manufacture the microfluidic chips. The microfluidic chips utilized in this Example are made by isotropic etching (in HF) of a predetermined pattern of grooves into a quartz wafer substrate (about 1 mm thick) to a depth of about 12 microns by employing an etch mask width of 40 microns. The resulting groove has a widest dimension of about 64 microns. Enclosed channels are formed by fusing to the etched wafer surface a smooth, flat quartz wafer. The wafers are then diced into chips of desired size each incorporating one or more microchannels. Such microfluidic chips in general have at least one main channel and usually have one, or more, side channels that either add fluids to, or take fluids from, the main channel. The microfluidic chip utilized in this Example has two side channels at the proximal end of a main channel. In addition the example chip design incorporates a 20 micron diameter, ca. 2 cm long, capillary inserted at the proximal end of the main microchannel (at an angle perpendicular to the plane of the microchannel). The protruding capillary facilitates sipping of liquids from small sample wells such as the wells of a standard 96 or 384 well microplate. The two side channels at the proximal end of the main channel have identical cross-sectional dimensions as the main channel. The hydrodynamic resistances of the channels and capillary are determined by their length and are such that when equal viscosity materials are present in each, about 80% of the volume in the distal end of the main channel is supplied from the capillary and 10% is supplied from each of the side-channels when a small vacuum, such as −1 to −2 psi is applied to the distal end of the main channel.

Prior to applying the Ludox AM-30 colloidal particles to the microfluidic chip, the suspension was first diluted to a desired concentration from 30% by wt. (16.3% volume/volume) into a buffer comprising 100 mM pH 7.5, sodium HEPES. In an experiment designed to test the particle concentration needed to prevent protein binding to the interior surface of microchannels, various dilutions of the colloidal particles suspension were combined in equal volume with 1.22 micromolar protein-kinase A, type-beta, (PKA-β) enzyme in the same buffer containing 5 mM MgCl. The resulting suspension of colloidal particles and protein were added to a well fluidically connected to one side-channel of the microchip leading to a proximal part of the main channel (near the intersection of the capillary and channel). Substrates for the enzyme were added to a second well fluidically connected to a second side-channel which intersected the main channel, just distal to its intersection point with the first side-channel. The substrates included about 10 micromolar adensosine triphosphate (ATP) and a fluorescent substrate of the kinase enzyme, all dissolved at a concentration of about 10 micromolar in the 100 mM, pH 7.5, sodium HEPES buffer containing 5 mM MgCl, so that enzyme activity could be monitored in the main channel, as described in Example 1 and further described in: A. W. Chow, A. R. Kopf-Sill, T. Nikiforov, A. Zhou, J. Coffin, G. Wada, M. Spaid, Y. Yurkovetsky, S. Sundberg and J. W. Parce, "High Throughput Screening on Microchips," Micro Total Analysis Systems 2000, ed. A. van den Berg, W. Olthuis and P. Bergveld, 489-492, Kluwer Academic Publishers, the Netherlands, 2000, which is incorporated by reference herein. An even more detailed description of the method, with multiple examples, can be found in the "User's Manual for the Caliper 250 HTS System," available commercially from Caliper Technologies Corporation.

After the enzyme activity was monitored with the highest concentration of colloidal particles (together with enzyme) in the first well, the contents of the first well were removed and rinsed several times with the buffer and the enzyme activity was again monitored without enzyme in the buffer. Any presence of remaining enzyme activity in the main channel, at this time, indicated that the enzyme had previously bound to the surface of the main microchannel and had remained active. Absence of enzyme activity at this time, in contrast, was taken as an indication that active enzyme was not bound to the main channel walls. This process was repeated for each dilution of colloidal particles in order to determine the concentration of particles required to prevent the protein enzyme from binding to the microchannel interior surfaces.

No residual enzyme sticking was observed at an initial concentration of 0.24 wt. % colloidal particles (0.024 wt. % after dilution into the main channel). At 0.03% wt. % (0.003 wt. % in the main channel) a slight amount of residual enzyme binding to the main channel wall was observed. At 0.01% wt. % (0.001 wt. % in the main channel) a substantial fraction of the enzyme was found to be bound to the main channel wall. Because colloidal silica has a density of about 2.2 g/cc and water has a density of about 1.0 g/cc, the corresponding volumetric concentrations of particles are obtained by dividing by 2.2. Thus, a concentration of between about 0.003 wt. % (0.0014 vol. %) and 0.024 wt. % (0.011 vol. %) colloidal particles in the main channel was needed to prevent protein sticking to the main channel surface.

Apparently, a minimal ratio of colloidal particle surface area-to-channel surface area must be maintained in order to prevent protein sticking to the microchannel surfaces. One may compute the surface area of the particles and the microchannels. This calculation is particularly straightforward if the particles are spherical and the cross-section of the microchannels is circular. Otherwise this ratio may be estimated without much error by taking appropriate geometrical factors (and if significant, surface roughness) into account. For the example, the microchannels used in the present Example were made by isotropic etching of a quartz substrate (e.g. with BF) to about 12 microns in depth, employing a mask width of 40 microns, the resulting etched groove has a width of about 64 microns at the top and a flat bottom width equal to the mask width. When a smooth top member is fused to the etched substrate, the resulting enclosed microchannel has a volume and surface area as follows:

$$\text{Surface Area}=\{[(\text{Mask Width})+[(2+\pi)(\text{Depth})]]\}*\text{Length} \quad \text{(Eq. 1)}$$

$$\text{Volume}=\{[(\text{Mask Width})(\text{Depth})]+[\pi/2(\text{Depth})^2]*\text{Length} \quad \text{(Eq. 2)}$$

The resulting ratio of surface area to volume is:

$$\text{Surface Area/Volume}=[2+\pi+(\text{Mask Width/Depth})]/[(\text{Mask Width})+(\pi/2\ \text{Depth})] \quad \text{(Eq. 3)}$$

For the microchannel used in this Example, the depth is 12 microns and the mask width is 40 microns. Thus, the channel surface area is about 102 square microns per micron channel length and the volume is about 706 cubic microns per micron channel length. Consequently the ratio of channel surface area to volume ($CH_{(A/V)}$) is about 0.144 microns$^{-1}$. For generally spherical particles with radius r, the surface area is about 4 $\pi r^2$ and the volume is about 4/3 $\pi r^3$. Thus the ratio of particle surface area to volume ($P_{(A/V)}$) is just 3/r. That is, the volume is equal to r/3 times the surface area. The ratio of particle surface area/channel surface area, therefore, is given as:

$$R=C_V(P_{AV}/CH_{A/V}) \quad \text{(Eq. 4)}$$

where $C_V$ is the volumetric concentration of colloidal particles. Therefore the lowest effective range of particle surface area to channel surface area may be determined from the data in the above example, where ($P_{(A/V)}$) is 3/r, r is 0.006 microns, $CH_{(A/V)}$ is 0.144 microns$^{-1}$. From Eq. 4 above and the finding that the effective $C_V$ is found to be between 0.011 vol. % from 0.0014 vol. % in the main channel, the lowest effective range of particle surface area to channel surface area is found to be between 0.54 and 38. Thus, the surface area of the required particles is about equal to the surface area of the channel.

The surface area/volume of spheres is inversely proportional to the particle radius. Since roughly 0.01 to 0.001 volume % of the 0.006 micron radius particles was required to prevent protein sticking in such microchanmels; and since the radius of colloidal particles generally ranges from about 0.0006 microns to about 0.6 microns, the relative volume of particles useful in the method will generally range from about 0.0001 volume % to about 1%. There did not appear to be any deleterious effect of excess particle surface area. Thus the maximum concentration of particles is not limited, except by practical considerations such as the effect of the particles in increasing viscosity at very high concentrations. Thus the maximum concentration could be very high, for example ranging from 50% to 90% or greater.

In summary, the colloidal particles generally will be used at a given concentration suspended in a liquid that is to be delivered into a microchannel. The concentration of the particles suspended in the liquid may be such that the surface area of the particles contained in a given volume of liquid is equal to, or greater than, the surface area of a channel needed to contain the liquid volume. For example, the surface area of the particles contained in a given volume of liquid may vary between about 10 and $10^6$ times the surface area of the microchannel. Supplying the colloidal particles so that their surface area is about 10 times the surface area of the microchannels is believed to be preferable, though the present invention is in no way is to be limited to such teaching. If the particles are diluted by merging with streams without the particles, then the original concentration of particles should be correspondingly increased by the dilution factor so as to keep the particle surface area about equal to or in excess of the channel surface area. For example, for a 10-fold dilution performed in a microfluidic channel, would then dictate that the particle concentration should be increased by a factor of about 10 (or greater).

Example 3

Colloidal silica particles as described above in Example 1 were again diluted 1:1 with pH 7.5 sodium HEPES buffer and then mixed with equal volume of 1.22 micromolar solution of protein kinase-A-β enzyme (PKA-β) in the same buffer. The mixture containing enzyme and 7.5% colloidal silica was placed into each of four enzyme wells of a sample microfluidic assay chip and the inhibitors again were assayed as described previously. The addition of the colloidal particles to the microfluidic microchannels having adsorbed enzyme removed the enzyme activity from the walls, leaving the walls free of such activity. Thus, colloidal particles can be used intermittently (or continuously) between successive inhibitor assays so as to remove enzyme residue and clean the walls to leave a clean surface for each assay. Intermittent injection of the colloidal silica particles can be accomplished by standard microfluidic techniques including multiport pressure control or electroosmotic flow induced by electrical potential switching as described previously, or alternatively by a physical valve which opens and closes to provide for flow of particles into the assay microfluidic conduit.

Unless otherwise specified, all concentration values provided herein refer to the concentration of a given component as that component was added to a mixture or solution independent of any conversion, dissociation, reaction of that component to alter the component or transform that component into one or more different species once added to the mixture or solution.

The method steps described herein are generally performable in any order unless an order is specifically provided or a required order is clear from the context of the recited steps. Typically, the recited orders of steps reflects one preferred order.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications and patent documents cited in this application are incorporated by reference in their entirety for all purposes to the same extent as if each individual publication or patent document were so individually denoted.

What is claimed is:

1. A method of removing a residue of one or more biological materials deposited on an interior surface of a microchannel, the method comprising flowing a colloidal system through a microchannel, the system comprising colloidal particles in a fluid at a sufficient concentration to adsorb to a surface of the one or more materials and thereby remove the residue of the materials from the microchannel interior surface.

2. The method of claim 1 wherein said colloidal particles comprise colloidal silica particles.

3. The method of claim 2 wherein said colloidal silica particles have a surface area of greater than about 200 square meters per gram of solid particle.

4. The method of claim 1 wherein the colloidal particles comprise one or more of colloidal alumina, silicon nitride, and magnesium oxide particles.

5. The method of claim 1 wherein the colloidal particles comprise organic polymer colloidal particles.

6. The method of claim 5 wherein said organic polymer colloidal particles comprises polyethylene or polystyrene particles.

7. The method of claim 1 wherein said colloidal system is periodically or continuously administered into the microchannel.

8. The method of claim 1 wherein the colloidal particles have a major dimension in the range of about 1 millimicron to about 1 micron.

9. The method of claim 1 wherein the colloidal particles are present in the fluid at a concentration of between about 0.0001 and 1% by volume.

10. The method of claim 1 wherein the colloidal particles are present in the fluid at a concentration of greater than about 0.024% by weight.

11. The method of claim 1 wherein the colloidal particles are present in the fluid at a concentration of greater than about 0.003% by weight.

12. The method of claim 1 wherein the colloidal particles are present in the fluid at a concentration of between about 0.003 and 0.024% by weight.

13. The method of claim 1 wherein the concentration of colloidal particles in the fluid is such that a surface area of the particles contained in a given volume of the fluid is equal to or greater than a surface area of the microchannel.

14. The method of claim 1 wherein said one or more biological materials comprise one or more of a protein, a cell, a carbohydrate, a nucleic acid and a lipid.

* * * * *